US010379011B2

(12) United States Patent
Brubacher

(10) Patent No.: US 10,379,011 B2
(45) Date of Patent: Aug. 13, 2019

(54) MICROORGANISM SORTING SYSTEM AND METHOD

(71) Applicant: SoBru Solutions, Inc., Fullerton, CA (US)

(72) Inventor: John Miles Brubacher, La Mirada, CA (US)

(73) Assignee: SoBru Solutions, Inc., Fullerton, CA (US)

( * ) Notice: Subject to any disclaimer, the term of this patent is extended or adjusted under 35 U.S.C. 154(b) by 426 days.

(21) Appl. No.: 15/113,983

(22) PCT Filed: Jan. 23, 2015

(86) PCT No.: PCT/US2015/012768
§ 371 (c)(1),
(2) Date: Jul. 25, 2016

(87) PCT Pub. No.: WO2015/112910
PCT Pub. Date: Jul. 30, 2015

(65) Prior Publication Data
US 2016/0334308 A1 Nov. 17, 2016

Related U.S. Application Data

(60) Provisional application No. 61/931,412, filed on Jan. 24, 2014.

(51) Int. Cl.
G01N 1/20 (2006.01)
G01N 15/00 (2006.01)
G01N 15/14 (2006.01)

(52) U.S. Cl.
CPC ......... *G01N 1/2035* (2013.01); *G01N 15/147* (2013.01); *G01N 2015/0065* (2013.01)

(58) Field of Classification Search
USPC .......................................... 422/73
See application file for complete search history.

(56) References Cited

U.S. PATENT DOCUMENTS 5,299,141 A    3/1994  Hungerford et al.
5,763,794 A *  6/1998  Marrelli .................... G01F 1/46
                                                  324/640

(Continued)

FOREIGN PATENT DOCUMENTS

GB    2477075 A       7/2011
WO    2013172931 A1   11/2013
WO    2013192187 A9   12/2013

OTHER PUBLICATIONS

International Search Report and Written Opinion PCT/US2015/012768, dated Apr. 20, 2015.

*Primary Examiner* — Jill A Warden
*Assistant Examiner* — Brittany I Fisher
(74) *Attorney, Agent, or Firm* — Lodestone Legal Group; Jeromye V. Sartain

(57) ABSTRACT

A microorganism evaluation system comprising a first viewing section, wherein a first fluid flow supplies and passes through the first viewing section, the first fluid flow defining a first fluid flow rate, a relatively smaller second viewing section, wherein a second fluid flow supplies and passes through the second viewing section, the second fluid flow defining a second fluid flow rate, and an isokinetic probe positioned so as to sample from the first fluid flow so as to provide the second fluid flow.

20 Claims, 9 Drawing Sheets

(56) References Cited

U.S. PATENT DOCUMENTS

| | | | |
|---|---|---|---|
| 5,894,080 A | 4/1999 | Dybdahl | |
| 6,742,404 B2* | 6/2004 | Smith | G01N 1/14 |
| | | | 73/863.03 |
| 7,900,780 B2 | 3/2011 | Ueki et al. | |
| 2002/0036167 A1* | 3/2002 | Mayeaux | G01N 1/2035 |
| | | | 210/637 |
| 2007/0137314 A1* | 6/2007 | Watson | G01N 1/38 |
| | | | 73/863 |
| 2007/0193373 A1* | 8/2007 | Xie | B01F 5/0682 |
| | | | 73/863.03 |
| 2010/0145634 A1* | 6/2010 | Pinguet | G01F 1/46 |
| | | | 702/45 |

* cited by examiner

MICROORGANISM SORTING SYSTEM AND METHOD

RELATED APPLICATIONS

This application claims priority and is entitled to the filing date of U.S. Provisional application Ser. No. 61/931,412 filed Jan. 24, 2014, and entitled "Microorganism Sorting System and Method." The contents of the aforementioned application are incorporated herein by reference.

INCORPORATION BY REFERENCE

Applicant hereby incorporates herein by reference any and all patents and published patent applications cited or referred to in this application.

TECHNICAL FIELD

Aspects of this invention relate generally to microorganism sorting systems and methods, particularly a system and method for physically separating microorganisms within a fluid into two or more flows and associated evaluation systems.

BACKGROUND ART

By way of background, a number of industries are affected by regulations relating to water treatment, such as ballast water treatment systems ("BWTS") on ships and the like. Such regulations require that microorganisms be effectively treated (killed) by the BWTS before such water is returned to the ocean or other body of water. Generally speaking, Zooplankton in the size range of approximately 10 to 50 microns is an "indicator" microorganism used to determine the effectiveness of treatment, though it will be appreciated that other organisms in alternative size ranges are possible depending on the context and other factors, such that organisms greater than 50 microns may also be the "indicators." In the art, monitoring of the effectiveness of such BWTS has largely been handled through samples submitted to a lab, there most often involving human examination under a microscope. Such approaches to compliance assessment have numerous shortcomings in terms of accuracy, speed, and cost. Similarly, flow cytometry systems, though typically offering relatively higher throughput, are also lacking in terms of viability determination (determinations regarding whether an organism is living) and portability for field or deployed uses. Applicant has already made improvements over such prior art systems by developing new and novel evaluation systems and methods for determining whether microorganisms are living, such as disclosed in pending international patent application Ser. No. PCT/US2013/046334 filed Jun. 18, 2013, and U.S. provisional patent application Ser. No. 61/661,011 filed Jun. 18, 2012, to which the '334 international application claims priority, both entitled "Microorganism Evaluation System," and further related to obtaining samples of such organisms from or within fluid flows as disclosed in pending international patent application Ser. No. PCT/US2014/029428 filed Mar. 14, 2014, and U.S. provisional patent application Ser. No. 61/782,937 filed Mar. 14, 2013, to which the '428 international application claims priority, both entitled "Sample Acquisition System and Method of Use," and further related to organism stimulation and image acquisition within an evaluation system as disclosed in pending international patent application Ser. No. PCT/US2014/070420 filed Dec. 15, 2014 and entitled "Microorganism Evaluation System," and U.S. provisional patent application Ser. No. 61/916,343 filed Dec. 16, 2013 and entitled "Microorganism Evaluation System Viewing Section," to which the '420 international application claims priority. The contents of the aforementioned applications are incorporated herein by reference. It is specifically noted that the applications entitled "Sample Acquisition System and Method of Use" are particularly directed to a means of effectively sorting live organic material from inorganic and dead organic material as compared to the present invention enabling sorting of or between live organisms.

DISCLOSURE OF INVENTION

Aspects of the present invention teach certain benefits in construction and use which give rise to the exemplary advantages described below.

The present invention solves the problems described above by providing new and novel improvements in or relating to such microorganism evaluation systems particularly relating to sorting organisms based on size or other characteristics indicative of or relating to motile response, as discussed in detail below.

A primary objective inherent in the above described system and method of use is to provide advantages not taught by the prior art.

Another objective is to provide a microorganism evaluation system comprising a first viewing section, wherein a first fluid flow supplies and passes through the first viewing section, the first fluid flow defining a first fluid flow rate, a relatively smaller second viewing section, wherein a second fluid flow supplies and passes through the second viewing section, the second fluid flow defining a second fluid flow rate, and an isokinetic probe positioned so as to sample from the first fluid flow so as to provide the second fluid flow.

Another objective is to provide such a microorganism evaluation system wherein the first fluid flow rate is greater than the second fluid flow rate.

Another objective is to provide a method of sorting microorganisms comprising the steps of: supplying a first fluid flow to a first viewing section, the first fluid flow defining a first fluid flow rate; sampling the first fluid flow through an isokinetic probe positioned therein, a probe fluid flow passing through the probe defining a probe fluid flow rate; and supplying a second fluid flow to a second viewing section, the second fluid flow defining a second fluid flow rate that is less than the first fluid flow rate.

It will be appreciated by those skilled in the art that the exact configuration of the apparatus may take a number of forms to suit particular applications without departing from the spirit and scope of the present invention. Accordingly, it will be further appreciated that the configuration of the apparatus shown and described is exemplary and that the invention is not so limited.

Other features and advantages of aspects of the present invention will become apparent from the following more detailed description, taken in conjunction with the accompanying drawings, which illustrate, by way of example, the principles of aspects of the invention.

BRIEF DESCRIPTION OF DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

MODES FOR CARRYING OUT THE INVENTION

The above described drawing figures illustrate aspects of the invention in at least one of its exemplary embodiments, which are further defined in detail in the following description.

Figure 1:
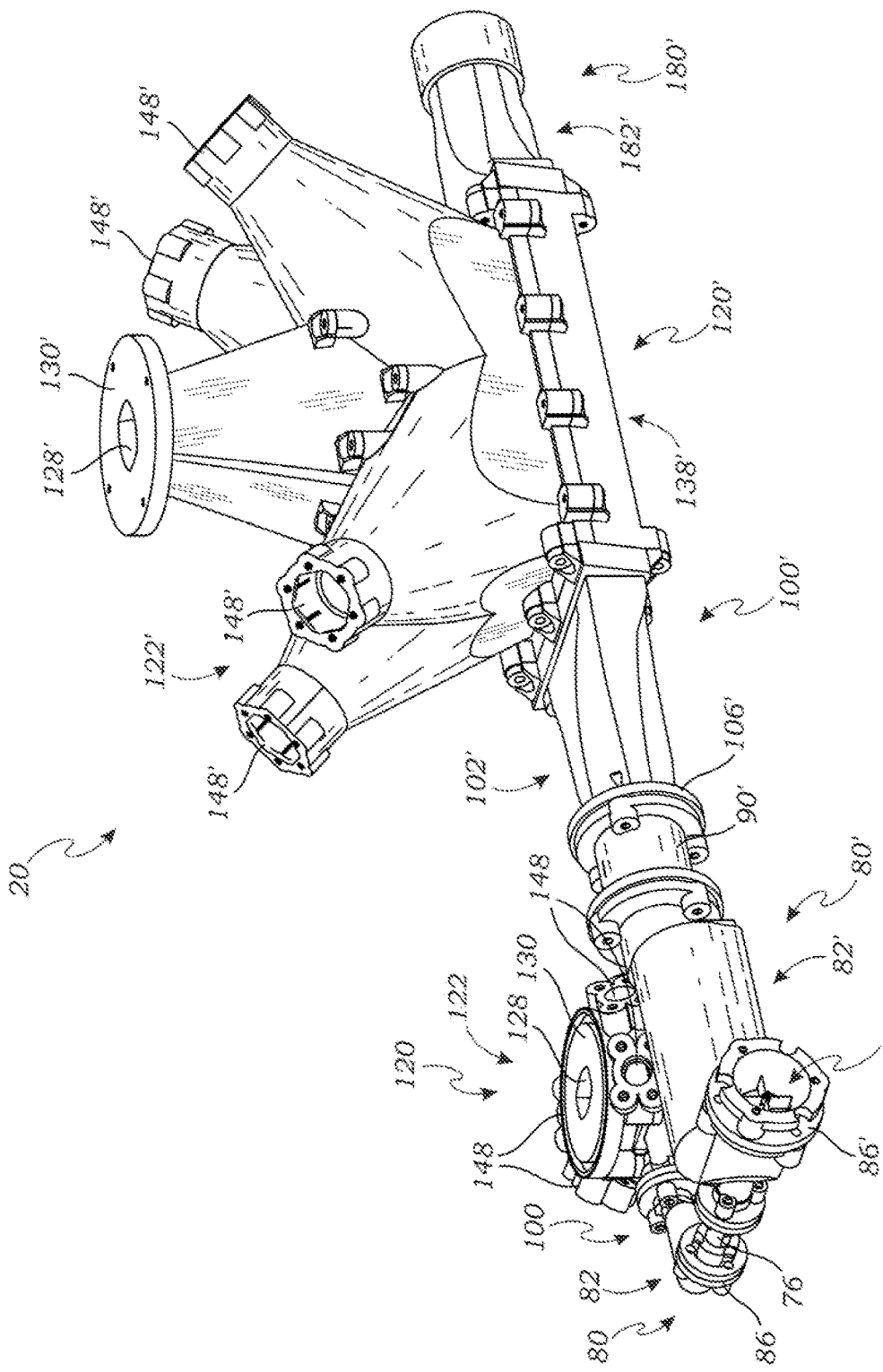
FIG. 1 is a perspective view of an operative portion of an exemplary microorganism evaluation system, in accordance with at least one embodiment.

Turning now to FIG. 1, there is shown a perspective view of an operative portion of an exemplary microorganism evaluation system 20 according to aspects of the present invention. Fundamentally, it will be appreciated that in the exemplary embodiment of fluid flow sampling, the disclosed evaluation system 20 is directed to or embodies a method by which such a fluid flow is first acted on or subjected to some sort of input in order to stimulate or induce a motile response from living microorganisms within the flow, and then to visually observe and acquire image data relative to such a motile response for the purpose of determining whether any organisms within the fluid sample are living. The system 20 comprises, in the exemplary embodiment, a first or primary, relatively larger microorganism stimulation section 80' defining a disorientation spiral 82' that is itself effectively sampled by a secondary, relatively smaller microorganism stimulation section 80 defining a disorientation spiral 82, such sampling being as by isokinetic sampling, for example. Particularly, there is shown in the exemplary embodiment an isokinetic probe 300 positioned within the inlet end of the larger microorganism stimulation section 80' adjacent and partially formed in the associated first loop coupling 86' and configured to sample from the flow passing therethrough and deliver the sample to the smaller microorganism stimulation section 80, much more about the probe 300 in terms of its configuration and operation being said below.

Figure 2:
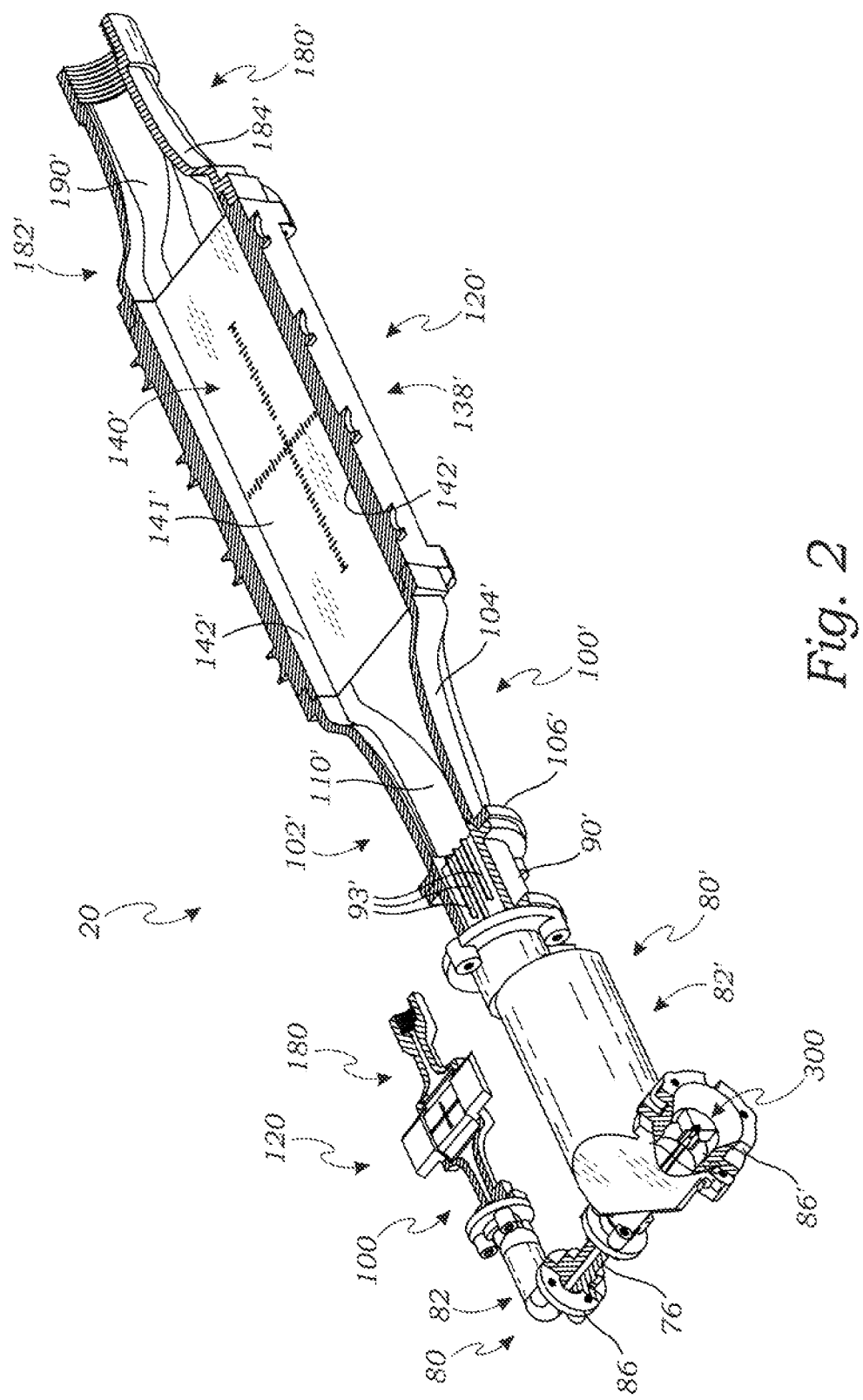
FIG. 2 is a partially sectioned perspective view thereof, in accordance with at least one embodiment.
Figure 3:
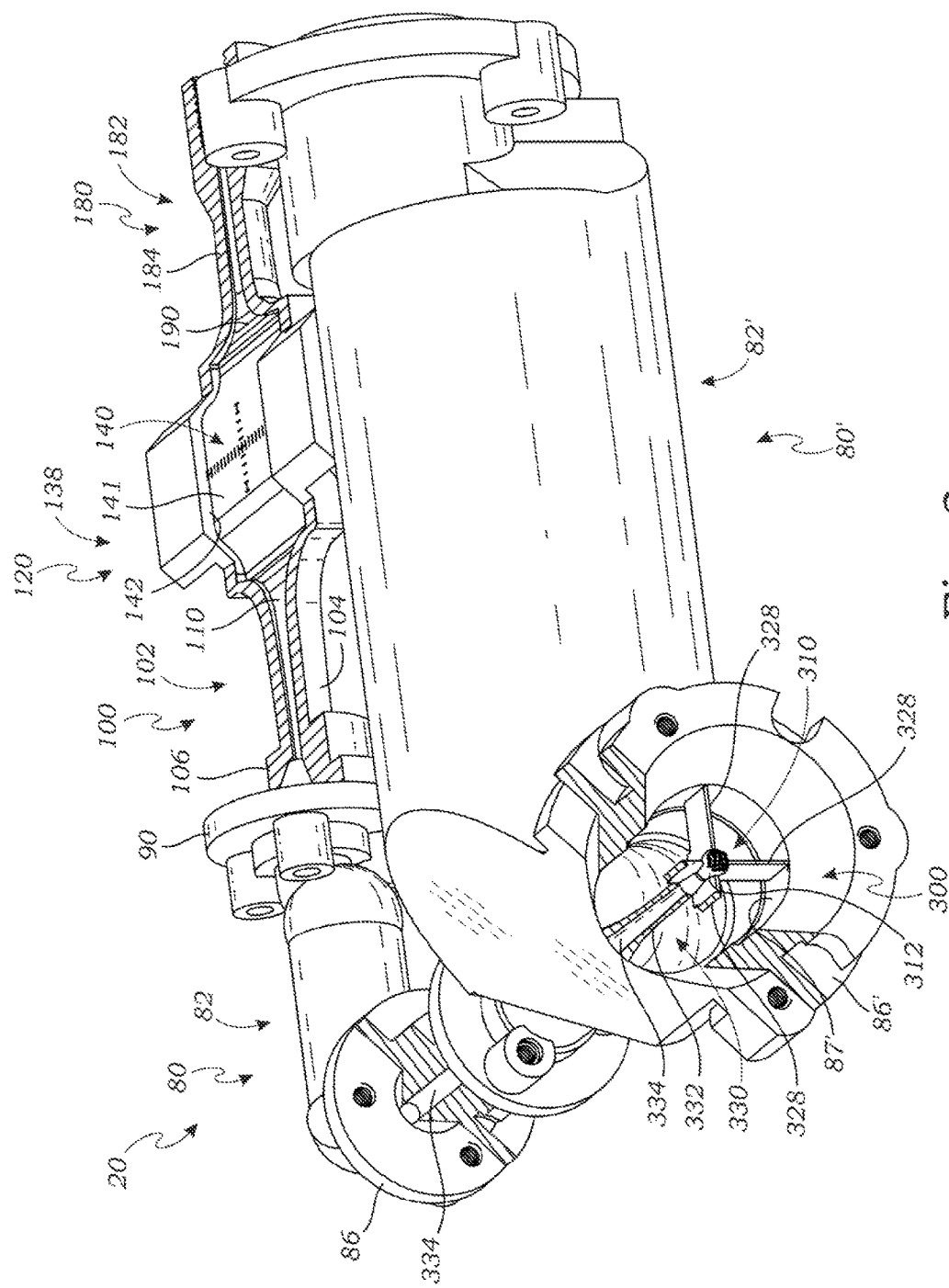
FIG. 3 is an enlarged partially sectioned partial perspective view thereof, in accordance with at least one embodiment.

With continued reference to FIG. 1 and further with reference to the partially sectioned perspective view of FIG. 2 and the enlarged partially sectioned partial perspective view of FIG. 3, within the off-line sampling portion of the microorganism evaluation system 20, which again as discussed further below sources its fluid flow through the isokinetic probe 300 positioned within the larger main-line sampling portion, from the smaller inertial stimulation section 80 the flow proceeds to a flow normalizing section 100 defining an inlet chute 102, such components being joined via coupling 90 of the stimulation section 80 and coupling 106 of the flow normalizing section 100. From the flow normalizing section 100, the flow continues into a viewing section 120. Within the viewing section 120 there is shown configured within the back plate 138 a back plate channel 140 through which the fluid flow passes formed from a channel bottom 141 and opposite channel side walls 142. Graduations or other such indicia may be formed on the channel bottom 141 for use in cooperation with the optical equipment (not shown) that would be mounted on the optical mount 130, with such optical equipment "seeing into" the viewing section 120 through the cavity first opening 128. Similarly, in the main fluid flow, from the larger inertial stimulation section 80' the flow proceeds to a flow normalizing section 100' defining an inlet chute 102', such components being joined via coupling 90' of the stimulation section 80' and coupling 106' of the normalizing section 100', and from the flow normalizing section 100' into a viewing section 120'. As with the smaller viewing section 120, the larger viewing section 120' may have configured within the back plate 138' a back plate channel 140' through which the fluid flow passes itself formed from a channel bottom 141' and opposite channel side walls 142', with graduations or other such indicia again being formed on the channel bottom 141'. Furthermore, it is noted with respect to the second loop coupling 90' that it may be formed internally with one or more baffles 93' so as to "straighten out" or render less turbulent the flow as it exits the stimulation section 80' and enters the flow normalizing section 100' or inlet chute 102'. It will be appreciated that any other such means now known or later developed for rendering a fluid flow relatively more laminar may be employed within the coupling 90' and/or in other locations within the system 20, including but not limited to the smaller coupling 90 of the off-line sampling portion, without departing from the spirit and scope of the invention. More generally, as shown, each viewing section 120, 120' comprises in the exemplary embodiment a viewing section body 122, 122' having an optical system mount 130, 130' and one or more illumination ports 148, 148', and an opposite back plate 138, 138' for completing and enclosing the viewing section 120, 120' inner space that defines the viewing port of each. As a threshold matter, it is to be understood that the illustrated hardware components—here essentially the microorganism stimulation section 80, 80', the flow normalizing section 100, 100', and the viewing section 120, 120', as well as the outlet section 180, 180' leading away from the viewing section 120, 120'—are merely representative or illustrative of aspects of the invention and are not limiting. Relatedly, it is to be expressly understood that while two portions of the overall microorganism evaluation system 20—a first, relatively larger main-line sampling portion having a first viewing section 120' and a second, relatively smaller off-line sampling portion having a second viewing section 120—are shown and described, the invention is not so limited, but may instead involve three or more separate viewing sections or sampling portions of varying geometries optimized for the variance in motile and other characteristics of the organisms that may be present in the system according to aspects of the present invention. Simply for illustration regarding scale in the exemplary embodiment, the larger stimulation section 80' helical flow path may have an inside diameter of approximately 16 mm feeding into a viewing section 120' that defines a flow cross-sectional area that is nominally 56.25 mm wide by 12 mm high or deep, as compared to the smaller sampling portion in which the stimulation section 80 may have a nominal inside diameter of 2.4 mm and a viewing section 120 that is nominally 20 mm wide by 3 mm high or deep. The resulting dual system 20 enables more throughput for use in contexts where larger volumetric or real-time sampling is desired as well as potentially enabling higher accuracy by secondary line sampling and evaluation within a viewing section 120 that has a nominal 3 mm depth of field while still allowing an acceptable aggregate throughput by employing the primary line having a nominal 12 mm depth of field, or a cross-sectional area of 675 mm$^2$ versus the 33.75 mm$^2$ of the secondary sampling line. It will once again be appreciated that such features may be combined in a variety of ways and employ a variety of sizes, shapes, and technologies now known or later developed without departing from the spirit and scope of the invention.

In the context of the present invention, it will be further appreciated with respect to the relative throughput of the relatively larger main-line viewing section 120' and of the relatively smaller off-line viewing section 120 that such functionality and capabilities enabled by varying the throughput in each also allows for more effective examination of microorganisms proportionately—that is, relatively smaller microorganisms can be more effectively analyzed in the relatively smaller viewing section 120 that has relatively slower flow rates and relatively larger microorganisms in the relatively larger viewing section 120' that has relatively higher flow rates. In a bit more detail, it is known that with certain environmental conditions motile-capable microorganisms will move on a substantially continuous basis. This motile activity is dependent on the right amount of stimulation, such as inertial excitation and/or the emission of light at a particular spectrum of energy (see Applicant's other co-pending applications for further details on such technologies or means of stimulating such microorganisms). The motile response of waterborne microorganisms is approximately correlated with body size, such that the amplitude of their response is roughly proportional to their size. As such, the velocity capability of microorganisms is similar over a range of organism sizes when using "variable-unit" velocities such as body-lengths (e.g., 10 body-lengths per second (bl/sec)). Whereas, it is generally known that larger organisms are able to move at greater "fixed-unit" velocities in comparison to smaller organisms. Using the 10 bl/sec velocity as an example, a 0.1 cm length microorganism would be able to move at an effective speed of 1 cm/sec (0.1 cm/bl×10 bl/sec), versus a relatively smaller 0.005 cm (50 micron) microorganism that would be able to move at an effective speed of only 0.05 cm/sec (0.005 cm/bl×10 bl/sec). Continuing with this example, then, and noting that the motile activity of waterborne microorganisms is approximately correlated with the local fluid velocity relative to the size of the microorganism, if a fluid flow rate having a local velocity of approximately 0.5 cm/sec is assumed, relatively larger microorganisms on the order of 0.1 cm in size are capable of a motile reaction against this fluid flow stimulation, while relatively smaller microorganisms on the order of 0.005 cm in size generally have a more limited motile reaction against this level of stimulation (i.e., are more likely swept along by such a fluid flow rather than being able to "swim" within or against it). It follows from the foregoing that fluid velocities in the respective viewing sections 120, 120' should be maintained below thresholds that might cause the microorganisms therein to be inhibited in their motile response characteristics; or, put another way, the microorganisms should be selected or sorted according to size as an indicator of the organisms' ability to exhibit a motile response within a particular fluid flow. As such, it will be appreciated that according to aspects of the present invention it is desirable to effectively "pair" microorganisms of certain sizes (or within certain size ranges) with a viewing section having a throughput or fluid flow velocity more appropriate for such microorganisms. Back to the exemplary geometries of the respective viewing sections 120, 120', then, the area available to observe motile response (viewing port) should be large enough to minimize the possibility of the microorganisms moving in and out of the viewing area but small enough, again, to provide the desired flow characteristics—generally, again, a relatively larger viewing section 120' or viewing port area for the larger microorganisms and a relatively smaller viewing section 120 or viewing port area for the smaller microorganisms. In addition, in the exemplary embodiment shown best in FIG. 2, the orientation of the aspect ratio is different between the small and large viewing sections 120, 120'. Specifically, the exemplary small viewing section 120 is 20 mm wide and only 11.25 mm long (or wider than it is long), while the large viewing section 120' is 56.25 mm wide and 100 mm long (or longer than it is wide). This feature supports further motile response measurement optimization. The larger chamber is longer than it is wide in order to provide a longer "field" for the relatively larger, and stronger microorganisms. The fluid velocity is greater, and combined with the length, should eliminate the possibility that these higher-energy microorganisms will be able to move in, and out, and back into the viewing chamber. In the case of the smaller viewing chamber, the smaller microorganisms don't have the energy to move in, and out, and back into the viewing chamber, but it is desirable to support a relatively higher fluid flow rate by using a relatively wider viewing chamber. Relatedly, the resulting measurement dwell time in the respective viewing sections 120, 120' will be long enough to adequately determine motile response depending on the fluid flow rate and the kinds of microorganisms within the flow, which dwell time is of course dependent on the geometry of the viewing section and the flow rate therethrough. In the exemplary embodiment of the evaluation system 20, an approximate range of dwell times might be from roughly 1 to 10 seconds, though those skilled in the art will appreciate that other dwell times above or below this range are possible and may even be preferable depending on a number of variables related to not only the viewing section configuration and the fluid flow rates and thus the types of microorganisms being evaluated but also the capabilities of the optical equipment and downstream data analysis equipment and software. Accordingly, it will be appreciated by those skilled in the art that a wide variety of viewing section configurations and related fluid flow characteristics are possible beyond those shown and described without departing from the spirit and scope of the present invention. More generally, it can be said that an aspect of the invention is that a relatively smaller viewing section or chamber will support a significantly lower fluid velocity so that relatively smaller microorganisms are not "overwhelmed" by the forces resulting from a higher flow rate, while a relatively larger viewing section or chamber will not only flow at a greater velocity, but the greater area will minimize the chance that a microorganism will move in and out of the viewing chamber.

Figure 4:
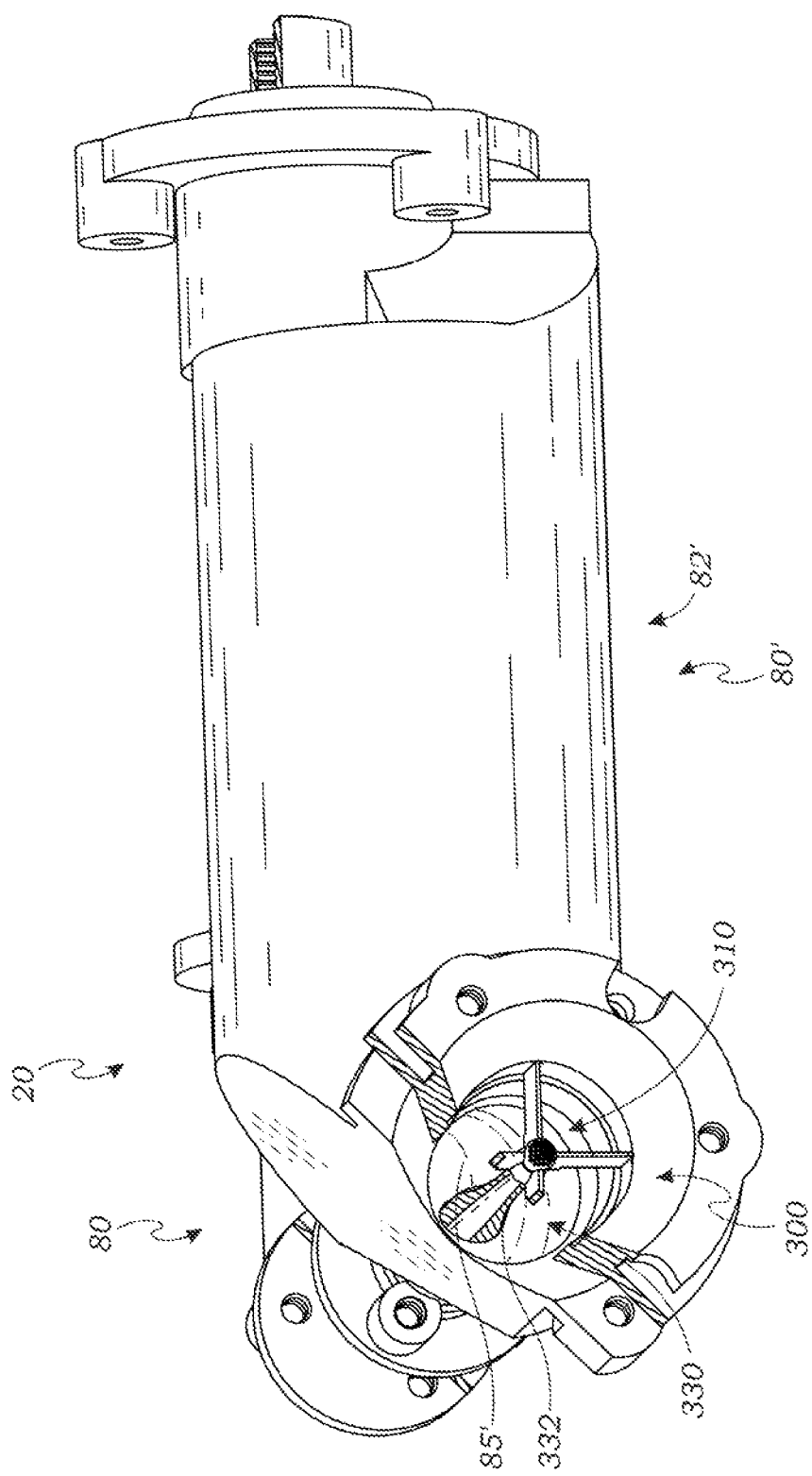
FIG. 4 is a further enlarged partially sectioned partial perspective view thereof similar to that of FIG. 3 and taken from a different perspective.
Figure 5:
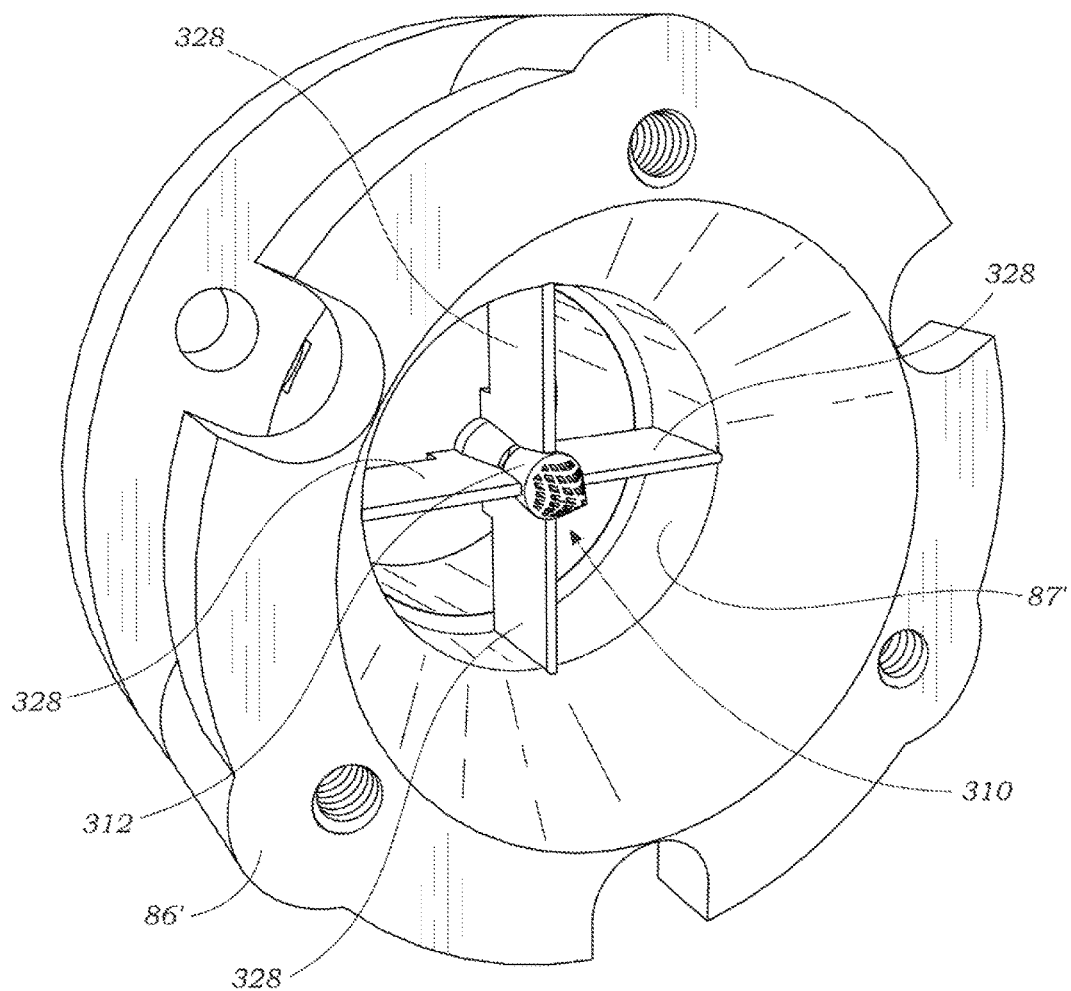
FIG. 5 is an enlarged perspective view of a component thereof, in accordance with at least one embodiment.

Next we turn to the exemplary means of thus sorting microorganisms based on size or body length so as to direct certain organisms into certain viewing sections for the reasons stated above. Generally speaking, the fluid velocities within these components is greater than what is realized within the respective viewing section in order to support such things as adequate inertial stimulation and inhibiting the microorganisms from "grabbing" the surfaces of the inside walls. Referring still to FIG. 3 and now to FIG. 4 as well, there are shown enlarged partial perspective and sectional views of particularly the small and large stimulation sections 80, 80' and the isokinetic probe 300 positioned within or adjacent to the inlet of the large stimulation section 80' and communicating via the probe conduit 330 from the probe tip 310 to the small stimulation section 80. In a bit more detail, as best shown in FIG. 3, the isokinetic probe 300 first comprises the probe tip 310 that is effectively integrated within the first loop coupling 86' by way of one or more spars 328 connected between the tip body 312 and the coupling inner wall 87', more about which will be said below in connection with FIGS. 5-9. At the tip proximal end 316 (FIGS. 6-9) there is attached in fluid communication therewith a probe conduit 330 having a conduit wall 332 and an inner conduit bore 334 communicating therethrough. As best seen in FIG. 4, the conduit wall 332 intersects and effectively passes through the first loop inner wall 85' of the larger disorientation spiral 82' so as to then deliver a portion of the fluid flowing toward the larger disorientation section 80' instead into the smaller disorientation section 80 by way of the conduit bore 334. As shown in FIG. 3, the conduit bore 334 may continue through tubing 76 (FIGS. 1 and 2) and first loop coupling 86 so as to deliver the isokinetic sampled flow directly to the smaller disorientation section 80, or the probe conduit 330 may terminate short of and instead be in fluid communication with the tubing 76 and the downstream remainder of the smaller off-line sampling portion of the system 20. Those skilled in the art will appreciate that such distinctions about where one component stops and another starts or whether a fluid conduit is composed of one or multiple components is immaterial and that the invention may be practiced in all such ways now known or later developed for substantially achieving the described function without departing from its spirit and scope, such that the manner of configuring and assembling the components is to be understood as merely illustrative of features and aspects of the present invention and non-limiting. As such, it is to be understood that while the probe conduit bore 334 is shown as continuing through the tubing 76 to the smaller disorientation section 80 this is not required but could instead be accomplished by multiple components in providing what is effectively a single flow path or conduit bore 334 from the isokinetic probe tip 310 to the off-line sampling section of the system 20. It will be further appreciated with continued reference particularly to FIG. 4 that whatever flow is not routed into and through the isokinetic probe 300 will thus simply pass around or outside the probe tip 310 and probe conduit 330 and "turn right" into the larger disorientation spiral 82'. Again, those skilled in the art will appreciate more generally that all such sizes and shapes and configurations of such inlet and outlet components, generally directed to slowing the fluid flow as it enters the viewing section 120' and to speeding up the fluid flow as it leaves the viewing section 120', are possible in the present invention without departing from its spirit and scope.

Figure 6:
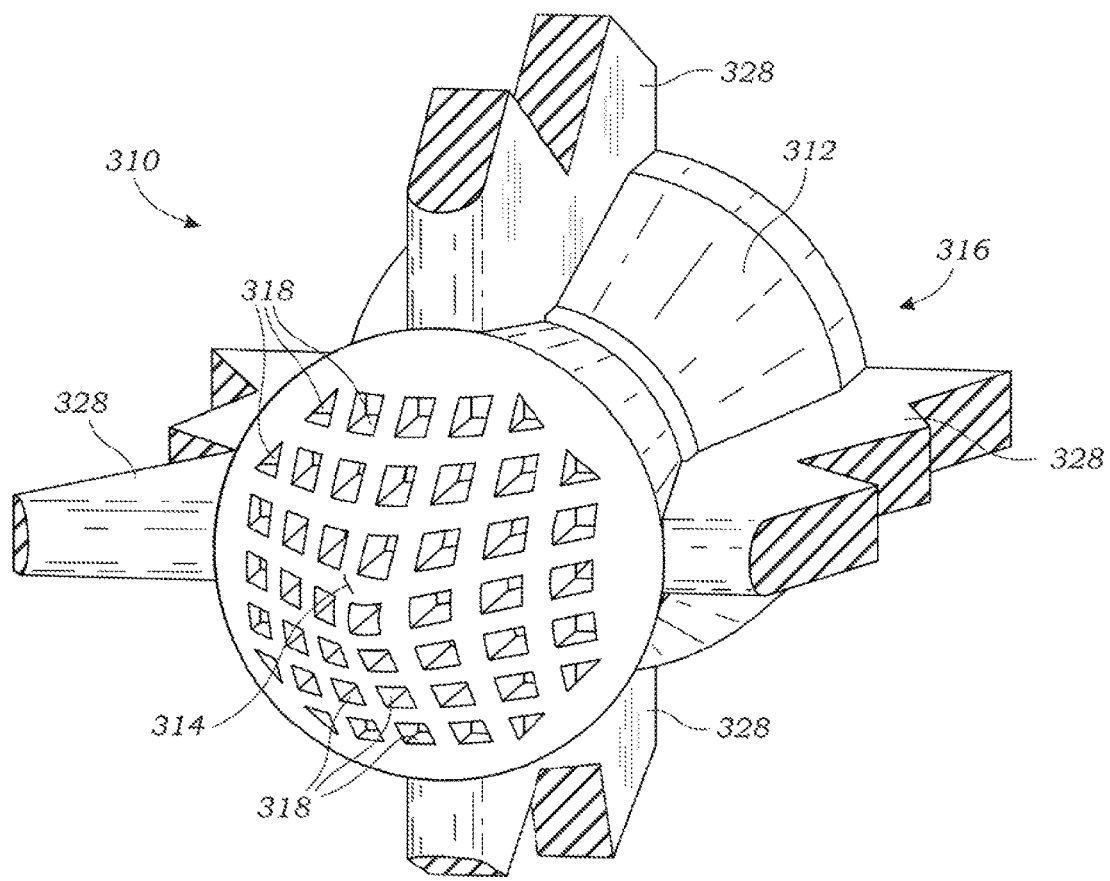
FIG. 6 is an enlarged partial perspective view of the component of FIG. 5, in accordance with at least one embodiment.

Turning now to FIGS. 5-9, there are shown enlarged partial perspective views so as to better appreciate particularly the features of the probe tip 310. First, in FIG. 5, it can again be seen that the probe tip 310 is effectively integrated within the first loop coupling 86' by way of one or more spars 328 connected between the tip body 312 and the coupling inner wall 87'. Once more, those skilled in the art will appreciate that other features of the first loop coupling 86' such as its outside surfaces, threaded and non-threaded mounting holes, and the like are all merely illustrative and non-limiting. Furthermore, and whether or not the design or configuration of the first loop coupling 86' changes, it will also be appreciated that the means of mounting or suspending the probe tip 310 within the coupling 86' may take a variety of other forms now known or later developed within the spirit and scope of the present invention, such as would be the case if the tip body 312 extended to and was mounted on the first loop inner wall 85' and picked up or interfaced with the probe conduit 330 at that point, such that the spars 328 would not be needed. Referring to FIG. 6, there is shown a further enlarged partial perspective view of the probe tip 310 now isolated from or "cut out of" the first loop coupling 86' (FIG. 5) so as to further focus in on the features of the probe tip 310 itself. As shown, particularly also in FIGS. 7 and 8, the distal surface 314 of the tip body 312 is substantially conical or cone-shaped and formed with a pattern of substantially parallel and substantially evenly distributed passages 318 therein so as to communicate with the interior of the probe tip 310 and ultimately the probe conduit 330, more about which will be said below. Those skilled in the art will appreciate that while particular sizes and shapes of the tip distal surface 314 and the tip passages 318 are shown, the invention is not so limited, but may instead involve a variety of other configurations without departing from its spirit and scope. More generally, it is noted that such a specially designed "screen" formed by the tip distal surface 314 and the tip passages 318 and positioned at the inlet to the isokinetic probe 300 serves as a means to sort the smaller microorganisms within the fluid flow from the larger. That is, the larger microorganisms will effectively be "blocked" from entering into the smaller viewing section 120, while the smaller microorganisms will flow through the "sorting screen" formed by the probe tip 310 and into the smaller viewing section 120. It is noted that a more complete evaluation of a microorganism's size would be based on, for example, a software algorithm's analysis of the irregular shape, not on mechanical means such as some form of a mesh screen as here. As such, the "screen" used at the intake of the present isokinetic probe 300, again here comprised of the tip distal surface 314 and the tip passages 318, will only effectively provide sorting of microorganisms and not a means to determine the "size" of any microorganism in the sense of a quantitative measurement. Relatedly, another means to sort the microorganisms is to generate a force or suction that will tend to "pull" organisms that are "weaker" into the smaller viewing section 120. The basic idea is to cause the inlet velocity in the probe 300 supplying the smaller viewing section 120 to be greater than the velocity of the adjacent fluid flow in the surrounding pipework supplying the main, larger viewing section 120'. Microorganisms tend to resist flowing into relatively confined areas such as the inlet into smaller pipework. Irrespective of size, stronger organisms may thus be able to resist the inlet flow into the smaller pipework, whereas weaker organisms will not. Accordingly, instead of or in cooperation with the geometry of the tip distal surface 314 and the tip passages 318, or instead of sorting only or primarily based on organism size as by using the probe as a "screen," it is further possible to sort organisms also based on their strength, with the relatively weaker and smaller organisms being pulled into the smaller viewing section 120 via the probe 300 while relatively stronger and larger organisms may resist flow into the probe 300 and so pass into the larger viewing section 120'. It will be appreciated from the above discussion that even relatively smaller organisms that are relatively stronger swimmers and so avoid the probe 300 and end up in the larger viewing section 120' will thus be capable of the requisite motile response while therein for purposes of image acquisition and viability assessment, which will generally be true of relatively larger organisms regardless, even if they are relatively weak swimmers for their size, with an important feature thus being that smaller and/or weaker organisms will generally end up in the smaller viewing section 120 where the flow rates are relatively lower and the desired image acquisition can still be achieved according to aspects of the invention. It should also be noted in this context that while the term "isokinetic probe" has been used throughout, which typically requires or is based on the premise that the flow rate within the probe inlet is substantially equal to that of the main fluid flow that is being sampled, that is not necessarily the case in the present invention, as follows from the foregoing.

Figure 7:
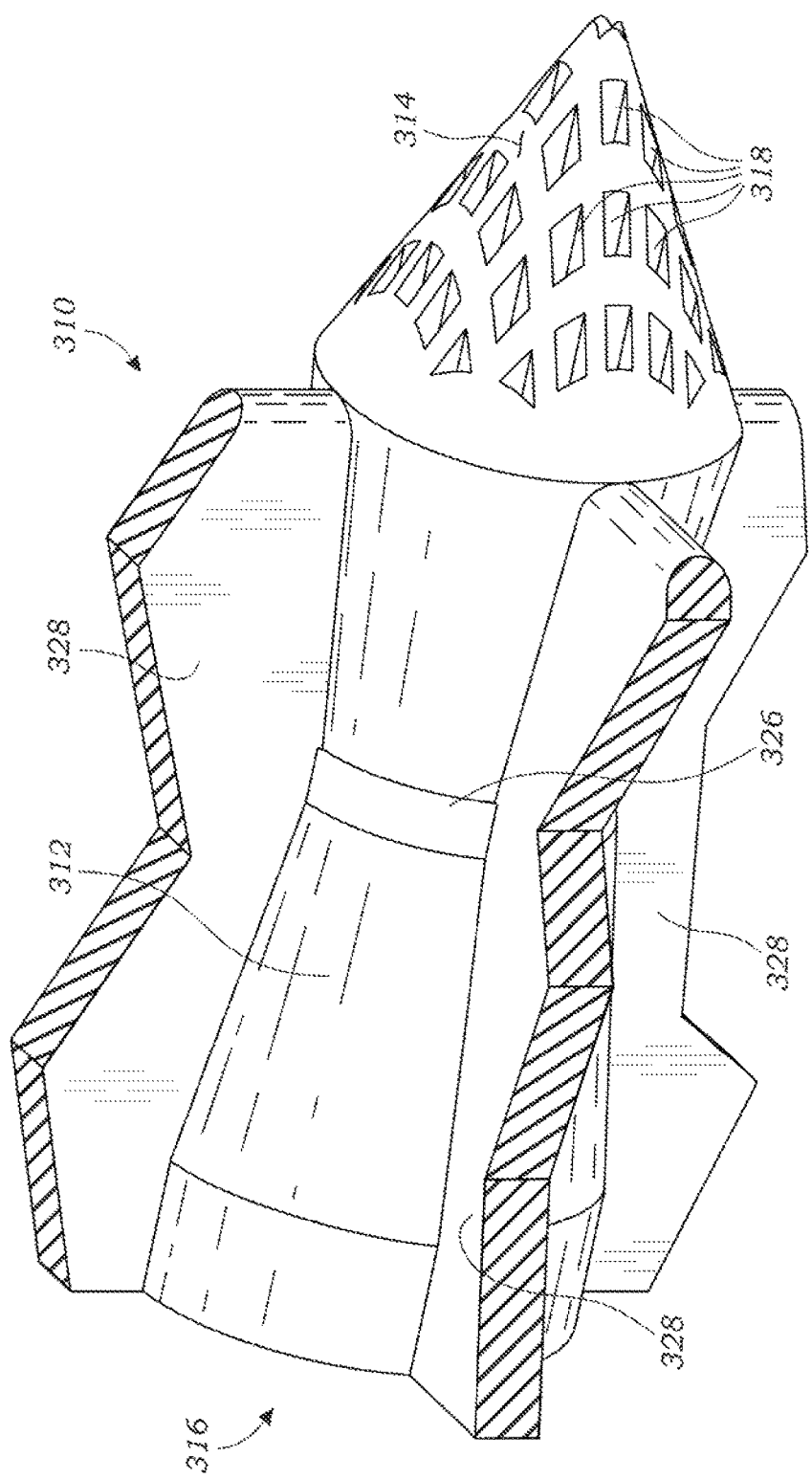
FIG. 7 is a side perspective view thereof, in accordance with at least one embodiment.
Figure 8:
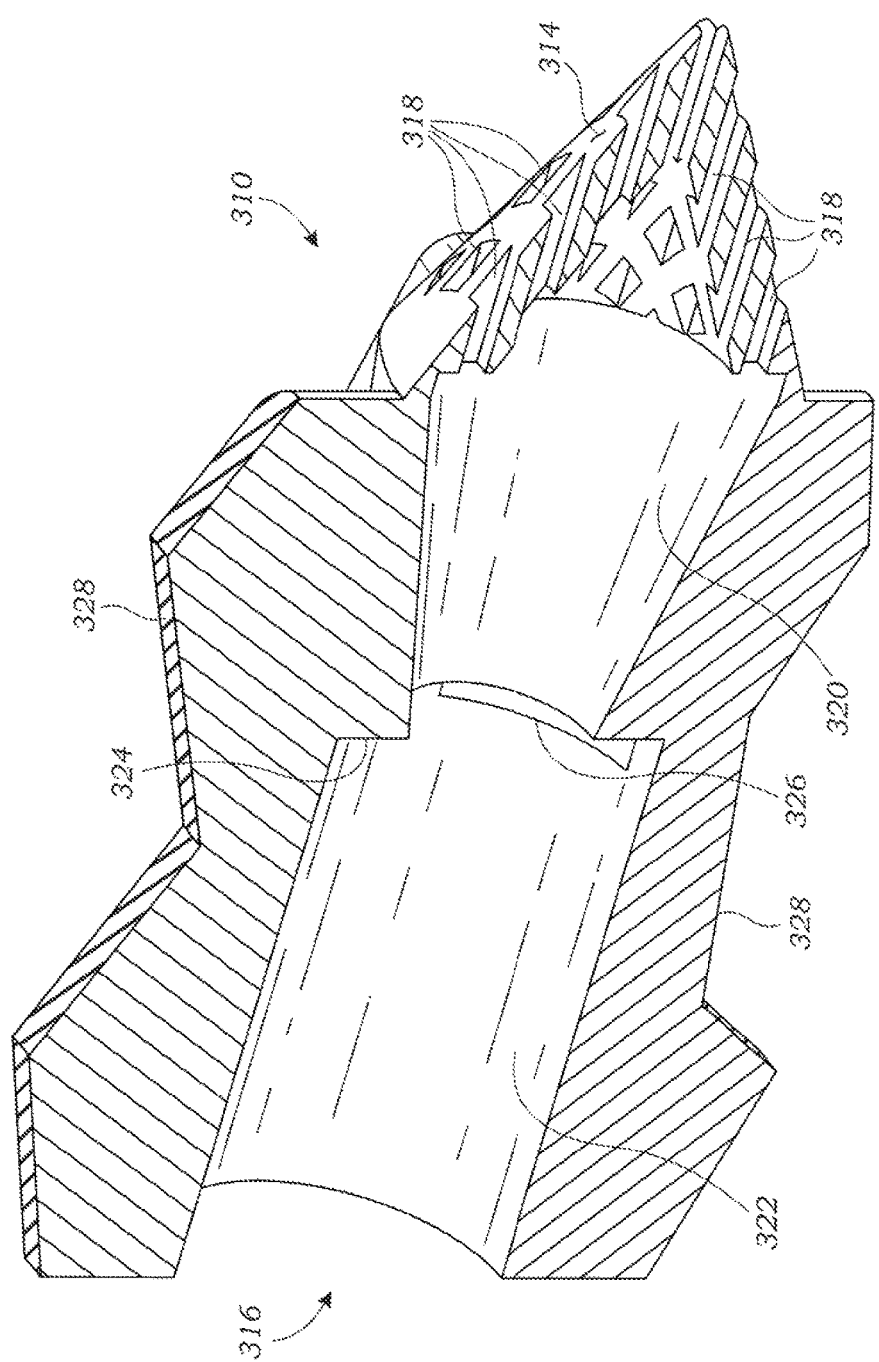
FIG. 8 is a sectioned side perspective view of the component of FIG. 7, in accordance with at least one embodiment.
Figure 9:
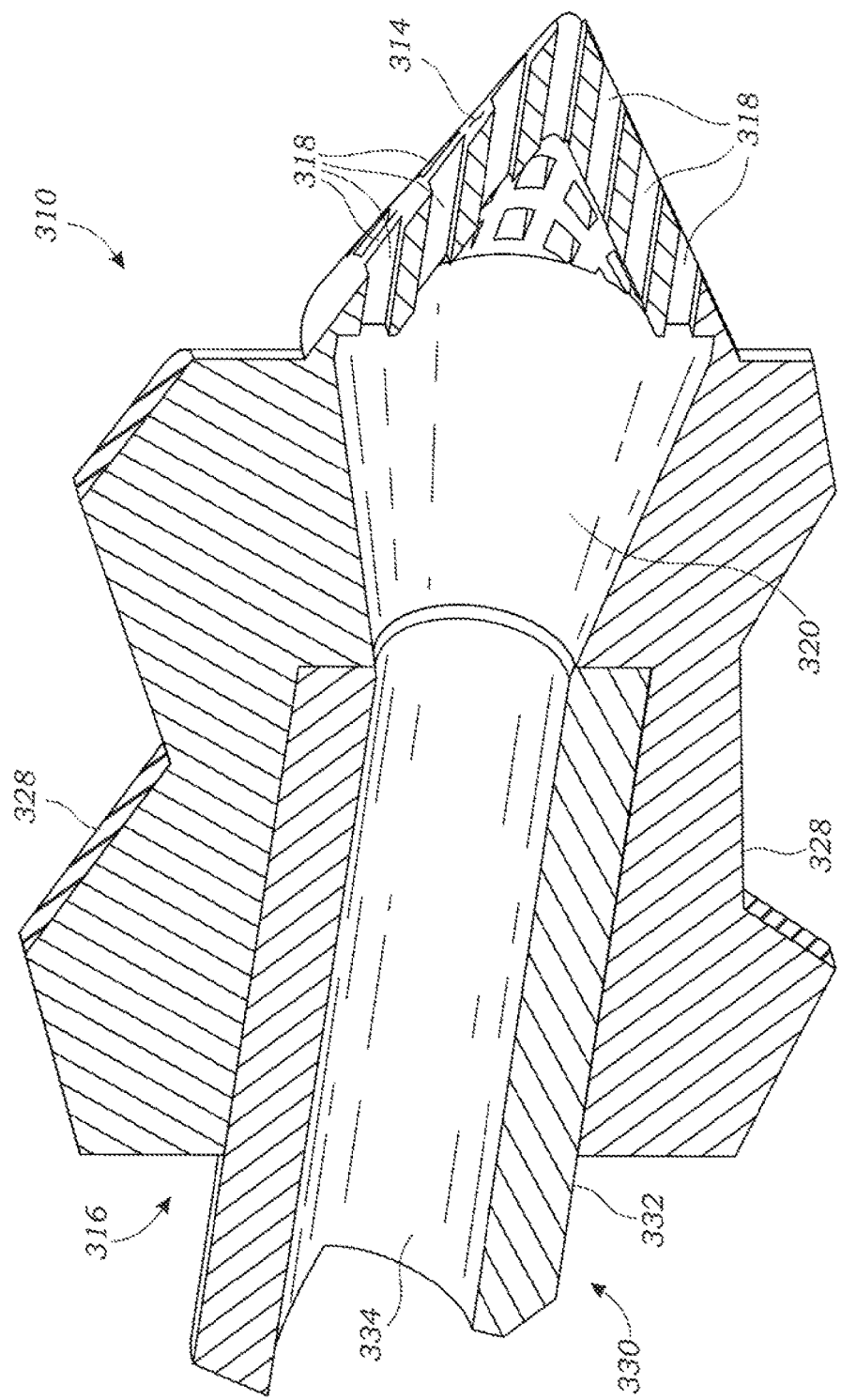
FIG. 9 is a further sectioned side perspective view analogous to FIG. 8, in accordance with at least one embodiment.

Referring now to FIGS. 7-9 particularly, where there are shown enlarged side perspective and sectioned perspective views of the probe tip 310, it will first again be observed that the tip distal surface 314, as best seen in these profile views, is in the exemplary embodiment substantially conical or cone-shaped, having a distal point and a circular base. It will thus be appreciated with respect to the above discussion regarding organism sorting through such a "screen" formed by the tip distal surface 314 and the tip passages 318 that the conical shape of the distal surface 314 will cause or assist the flow and any larger microorganisms not passing through the passages 318 to not be trapped or caught in the more traditional screen or mesh context, which "filters" or "sorters" eventually can become clogged and require cleaning, back-flushing, replacement, or other such maintenance, but instead to simply be blocked and "bounce off" the distal surface 314 and continue in the flow going around and past the isokinetic probe 300. The support spars 328 may also be formed with rounded leading edges as shown so as to further limit any disruption to the main fluid flow and any likelihood of actually trapping or catching organisms on the probe 300 or its support structure versus the flow and organisms entering or going by the probe 300. As best shown in FIG. 8, within the probe tip 310, or the tip body 312 more specifically, there is a tip first bore 320 in fluid communication with the tip passages 318 and a tip second bore 322 in fluid communication with the tip first bore 320, or between the tip first bore 320 and the tip proximal end 316. The tip first bore 320 is shown as being tapered from wide to narrow, or being larger at its entrance adjacent the tip passages 318 at the base of the distal surface 314 and smaller at its proximal end closer to the tip second bore 322. The tip second bore 322 is then shown as being generally larger than the tip first bore 320 so as to form a tip shoulder 324 therebetween and having a more constant diameter or, if anything, tapering slightly from narrow to wide, or being smaller at its entrance adjacent the tip first bore 320 and slightly larger at its exit at the tip proximal end 316. Accordingly, it will be appreciated that the tip second bore 322 is thus configured to accommodate the insertion of a tube or specifically the probe conduit 330, as best shown in FIG. 9, which conduit 330 may be inserted substantially to the full depth of the tip second bore 322 so as to stop or seat against the tip shoulder 324 formed at the distal end of the tip second bore 322 at the transition to the tip first bore 320.

It will be appreciated that preferably the conduit bore 334 at its distal end, or the end that is inserted within the tip second bore 322 of the probe tip body 312 is substantially equivalent to the diameter of the tip first bore 320 at its proximal end, or the end closest to the tip second bore 322 so as to provide a substantially smooth transition from the tip first bore 320 to the conduit bore 334. A chamfer may be formed at the inlet to the conduit bore 334 as shown, though this is not required. As also shown, best in FIG. 8, one or more tip slot 326 may be provided in the tip body 312 substantially at and communicating with the distal end of the tip second bore 322 so as to aid in assembly of the probe tip 310 or the probe conduit 330 with the probe tip 310. Those skilled in the art will appreciate that the tip slot 326 is to be sealed off when the probe 300 is assembled and, more generally, that all such geometric features are to be understood as merely exemplary and non-limiting. Regarding the more defined taper of the tip first bore 320, a further aspect of the present invention is to have the "screen" or the configurations of the tip distal surface 314 and the tip passages 318 and now the tip first bore 320 support a true isokinetic function wherein the sample that flows through the probe 300 to the smaller viewing section 80 is representative of the entire sample. In other words, the effective area of the inlet to the "screen," or that of the tip passages 318, will in the exemplary embodiment be equivalent to the required cross-sectional area to support isokinetic sampling. As a result, the actual cross-section of the inlet portion of the "screen" will be larger than the flow area of the isokinetic probe 300 in order to accommodate the geometrical requirements of a "mesh" design, or the tip passages 318 formed in the distal surface 314 of the probe tip 310. Then that enlarged area or cross-section will need to decrease back down to the true cross-sectional area needed for isokinetic sampling as essentially reflected in the probe conduit bore 334; hence, the decreasing taper within the tip first bore 320. It will be appreciated by those skilled in the art that a number of other geometrical designs and configurations of the probe 300 and probe tip 310 are thus possible without departing from the spirit and scope of the present invention, consistent with the above discussion wherein in an alternative embodiment the flow rate, by design, may be greater through the probe 300 than in the main pipe flow. Accordingly, a fundamental aspect of the present invention is how the "screen" in front of or leading into the isokinetic probe 300, as made up of the tip distal surface 314 and the tip passages 318, "blocks" but does not "catch" the relatively larger microorganisms and thereby supports the optimization of the viewing sections 120, 120' to better accommodate the different motile response characteristics between larger and smaller organisms.

Aspects of the present specification may also be described as follows:

1. A microorganism evaluation system comprising a first viewing section, wherein a first fluid flow supplies and passes through the first viewing section, the first fluid flow defining a first fluid flow rate, a relatively smaller second viewing section, wherein a second fluid flow supplies and passes through the second viewing section, the second fluid flow defining a second fluid flow rate, and an isokinetic probe positioned so as to sample from the first fluid flow so as to provide the second fluid flow.

2. The system of embodiment 1 wherein the first fluid flow rate is greater than the second fluid flow rate.

3. The system of embodiment 2 wherein the probe comprises a probe tip in fluid communication with a probe conduit, wherein a probe fluid flow passing through the probe tip and probe conduit defines a probe fluid flow rate.

4. The system of embodiment 3 wherein the probe fluid flow rate is substantially equal to the first fluid flow rate.

5. The system of embodiment 3 wherein the probe fluid flow rate is greater than the first fluid flow rate.

6. The system of embodiment 3 wherein the probe tip comprises a tip body having a tip distal surface and further comprises at least one tip passage communicating between the tip distal surface and the probe conduit.

7. The system of embodiment 6 wherein the probe tip comprises a plurality of substantially parallel tip passages, wherein the aggregate cross-sectional area of the tip passages is substantially equal to the cross-sectional area of the probe conduit.

8. The system of embodiment 6 wherein the tip body is formed having a tip first bore substantially corresponding to a conduit bore of the probe conduit.

9. The system of embodiment 8 wherein the tip body is formed having a tip second bore proximal of and substantially coaxial with the tip first bore, the tip second bore being larger than the tip first bore and substantially corresponding to a conduit wall of the probe conduit, the probe conduit seating against a tip shoulder formed between the tip first bore and the tip second bore, whereby a substantially constant flow path is formed between the tip first bore and the conduit bore.

10. The system of embodiment 9 wherein at least one tip slot is formed in the tip body substantially adjacent to the tip shoulder.

11. The system of embodiment 6 wherein the tip distal surface is substantially conical.

12. The system of embodiment 11 wherein a plurality of tip passages intersect the conical tip distal surface so as to effectively form a mesh screen that deflects rather than traps relatively larger organisms that do not pass through the tip passages, whereby the relatively larger organisms continue within the first fluid flow supplying the first viewing section and relatively smaller organisms pass into the second fluid flow supplying the second viewing section.

13. The system of embodiment 1 wherein: a first stimulation section defining a first inside diameter is in fluid communication with the first viewing section; a second stimulation section defining a second inside diameter is in fluid communication with the second viewing section; and the probe is positioned within the first stimulation section.

14. The system of embodiment 13 wherein the first inside diameter is at least five times greater than the second inside diameter.

15. The system of embodiment 14 wherein: the first inside diameter is about 16 mm; and the second inside diameter is about 2 mm.

16. The system of embodiment 1 wherein: the first viewing section defines a first flow cross-sectional area having a first width and a first height; the second viewing section defines a second flow cross-sectional area having a second width and a second height; and the first flow cross-sectional area is at least ten times greater than the second flow cross-sectional area.

17. The system of embodiment 16 wherein: the first flow cross-sectional area is defined by a first width of about 56 mm and a first height of about 12 mm; and the second flow cross-sectional area is defined by a second width of about 20 mm and a second height of about 3 mm.

18. The system of embodiment 16 wherein: the first flow cross-sectional area extends over a first length, wherein the first length is greater than the first width; and the second flow cross-sectional area extends over a second length, wherein the second length is less than the second width.

19. The system of embodiment 16 wherein: the first width is about 50 mm and the first length is about 100 mm; and the second width is about 20 mm and the second length is about 10 mm.

20. A microorganism evaluation system comprising: a first viewing section, wherein a first fluid flow supplies and passes through the first viewing section, the first fluid flow defining a first fluid flow rate; a relatively smaller second viewing section, wherein a second fluid flow supplies and passes through the second viewing section, the second fluid flow defining a second fluid flow rate, the second fluid flow rate being less than the first fluid flow rate; and an isokinetic probe positioned so as to sample from the first fluid flow so as to provide the second fluid flow, the probe comprising a probe tip in fluid communication with a probe conduit, wherein a probe fluid flow passing through the probe tip and probe conduit defines a probe fluid flow rate, the probe fluid flow rate being substantially greater than or equal to the first fluid flow rate.

21. A method of sorting organisms within a microorganism evaluation system, comprising the steps of: supplying a first fluid flow to a first viewing section, the first fluid flow defining a first fluid flow rate; sampling the first fluid flow through an isokinetic probe positioned therein, a probe fluid flow passing through the probe defining a probe fluid flow rate; and supplying a second fluid flow to a second viewing section, the second fluid flow defining a second fluid flow rate that is less than the first fluid flow rate.

22. The method of embodiment 21 wherein the probe fluid flow rate is substantially equal to the first fluid flow rate.

23. The method of embodiment 21 wherein the probe fluid flow rate is greater than the first fluid flow rate.

24. The method of embodiment 21 comprising the further step of sorting the organisms based on size as by configuring at least one tip passage within the probe so as to communicate between a tip distal surface and a probe conduit.

25. The method of embodiment 24 wherein the tip distal surface is substantially conical and a plurality of tip passages intersect the conical tip distal surface so as to effectively form a mesh screen that deflects rather than traps relatively larger organisms that do not pass through the tip passages, whereby the relatively larger organisms continue within the first fluid flow supplying the first viewing section and relatively smaller organisms pass into the second fluid flow supplying the second viewing section.

26. The method of embodiment 25 comprising the further step of pairing microorganisms of certain sizes with either the first viewing section or the second viewing section based on the tip passages relative to the organism sizes.

27. The method of embodiment 21 comprising the further step of pairing microorganisms of certain strengths with either the first viewing section or the second viewing section based on the respective first fluid flow rate and the second fluid flow rate relative to the organism strengths.

28. The method of embodiment 27 comprising the further step of selectively controlling the probe fluid flow rate relative to the first fluid flow rate.

To summarize, regarding the exemplary embodiments of the present invention as shown and described herein, it will be appreciated that a microorganism sorting system and method is disclosed and configured for separating relatively large and relatively small microorganisms within a fluid flow as by isokinetic sampling, screening, flow rate sorting, or any combination thereof so as to direct such organisms and their related flows to respective relatively large and small viewing sections for evaluation. Because the principles of the invention may be practiced in a number of configurations beyond those shown and described, it is to be understood that the invention is not in any way limited by the exemplary embodiments, but is generally able to take numerous forms in doing so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention. Furthermore, the various features of each of the above-described embodiments may be combined in any logical manner and are intended to be included within the scope of the present invention.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be expressly understood that the disclosed subject matter is in no way limited to a particular apparatus, methodology, configuration, size, shape, material of construction, protocol, etc., described herein, but may include any such technology now known or later developed without departing from the spirit and scope of the specification. Furthermore, the various features of each of the above-described embodiments may be combined in any logical manner and are intended to be included within the scope of the present invention. As such, various modifications or changes to or alternative configurations of the disclosed subject matter can be made in accordance with the teachings herein without departing from the spirit and scope of the present specification. Lastly, the terminology used herein is for the purpose of describing particular embodiments only, and is not intended to limit the scope of the present invention. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor believes that the claimed subject matter is the invention.

What is claimed is:

1. A microorganism evaluation system comprising:
a first viewing section, wherein a first fluid flow supplies and passes through the first viewing section, the first fluid flow defining a first fluid flow rate;
a relatively smaller second viewing section, wherein a second fluid flow supplies and passes through the second viewing section, the second fluid flow defining a second fluid flow rate that is less than the first fluid flow rate; and
an isokinetic probe positioned so as to sample from the first fluid flow so as to provide the second fluid flow, a probe fluid flow passing through the probe defining a probe fluid flow rate.

2. The system of claim 1 wherein:
the probe comprises a probe tip in fluid communication with a probe conduit, wherein the probe fluid flow passing through the probe tip and the probe conduit defines the probe fluid flow rate; and
the probe fluid flow rate is greater than or equal to the first fluid flow rate.

3. The system of claim 2 wherein the probe tip comprises a tip body having a tip distal surface and further comprises at least one tip passage communicating between the tip distal surface and the probe conduit.

4. The system of claim 3 wherein the probe tip comprises a plurality of substantially parallel tip passages, wherein the aggregate cross-sectional area of the tip passages is substantially equal to the cross-sectional area of the probe conduit.

5. The system of claim 3 wherein:
the tip body is formed having a tip first bore substantially corresponding to a conduit bore of the probe conduit; and
the tip body is formed having a tip second bore proximal of and substantially coaxial with the tip first bore, the tip second bore being larger than the tip first bore and substantially corresponding to a conduit wall of the probe conduit, the probe conduit seating against a tip shoulder formed between the tip first bore and the tip second bore, whereby a substantially constant flow path is formed between the tip first bore and the conduit bore.

6. The system of claim 5 wherein at least one tip slot is formed in the tip body substantially adjacent to the tip shoulder.

7. The system of claim 3 wherein the tip distal surface is substantially conical.

8. The system of claim 7 wherein a plurality of tip passages intersect the conical tip distal surface so as to effectively form a mesh screen that deflects rather than traps relatively larger organisms that do not pass through the tip passages, whereby the relatively larger organisms continue within the first fluid flow supplying the first viewing section and relatively smaller organisms pass into the second fluid flow supplying the second viewing section.

9. The system of claim 1 wherein:
a first stimulation section defining a first inside diameter is in fluid communication with the first viewing section;
a second stimulation section defining a second inside diameter is in fluid communication with the second viewing section; and
the probe is positioned within the first stimulation section.

10. The system of claim 1 wherein:
the first viewing section defines a first flow cross-sectional area having a first width and a first height;
the second viewing section defines a second flow cross-sectional area having a second width and a second height;
the first flow cross-sectional area extends over a first length, wherein the first length is greater than the first width; and
the second flow cross-sectional area extends over a second length, wherein the second length is less than the second width.

11. The system of claim 10 wherein:
the first width is about 50 mm and the first length is about 100 mm; and
the second width is about 20 mm and the second length is about 10 mm.

12. A microorganism evaluation system comprising:
a first viewing section, wherein a first fluid flow supplies and passes through the first viewing section, the first fluid flow defining a first fluid flow rate;
a relatively smaller second viewing section, wherein a second fluid flow supplies and passes through the second viewing section, the second fluid flow defining a second fluid flow rate, the second fluid flow rate being less than the first fluid flow rate; and
an isokinetic probe positioned so as to sample from the first fluid flow so as to provide the second fluid flow, the probe comprising a probe tip in fluid communication with a probe conduit, wherein a probe fluid flow passing through the probe tip and probe conduit defines a probe fluid flow rate, the probe fluid flow rate being substantially greater than or equal to the first fluid flow rate.

13. A method of sorting organisms within a microorganism evaluation system, comprising the steps of:
supplying a first fluid flow to a first viewing section, the first fluid flow defining a first fluid flow rate;
sampling the first fluid flow through an isokinetic probe positioned therein, a probe fluid flow passing through the probe defining a probe fluid flow rate; and
supplying a second fluid flow to a second viewing section, the second fluid flow defining a second fluid flow rate that is less than the first fluid flow rate.

14. The method of claim 13 wherein the probe fluid flow rate is substantially equal to the first fluid flow rate.

15. The method of claim 13 wherein the probe fluid flow rate is greater than the first fluid flow rate.

16. The method of claim 13 comprising the further step of sorting the organisms based on size as by configuring at least one tip passage within the probe so as to communicate between a tip distal surface and a probe conduit.

17. The method of claim 16 wherein the tip distal surface is substantially conical and a plurality of tip passages intersect the conical tip distal surface so as to effectively form a mesh screen that deflects rather than traps relatively larger organisms that do not pass through the tip passages, whereby the relatively larger organisms continue within the first fluid flow supplying the first viewing section and relatively smaller organisms pass into the second fluid flow supplying the second viewing section.

18. The method of claim 17 comprising the further step of pairing microorganisms of certain sizes with either the first viewing section or the second viewing section based on the tip passages relative to the organism sizes.

19. The method of claim 13 comprising the further step of pairing microorganisms of certain strengths with either the first viewing section or the second viewing section based on the respective first fluid flow rate and the second fluid flow rate relative to the organism strengths.

20. The method of claim 19 comprising the further step of selectively controlling the probe fluid flow rate relative to the first fluid flow rate.

* * * * *